United States Patent
Wong

(10) Patent No.: US 10,078,086 B2
(45) Date of Patent: Sep. 18, 2018

(54) USE OF INTERLEUKIN-27 AS A DIAGNOSTIC BIOMARKER FOR BACTERIAL INFECTION IN CRITICALLY ILL PATIENTS

(71) Applicant: Children's Hospital Medical Center, Cincinnati, OH (US)

(72) Inventor: Hector R. Wong, Cincinnati, OH (US)

(73) Assignee: Childrens Hospital Medical Center, Cincinnati, OH (US)

(*) Notice: Subject to any disclaimer, the term of this patent is extended or adjusted under 35 U.S.C. 154(b) by 59 days.

(21) Appl. No.: 14/424,919

(22) PCT Filed: Aug. 30, 2013

(86) PCT No.: PCT/US2013/057711
§ 371 (c)(1),
(2) Date: Feb. 27, 2015

(87) PCT Pub. No.: WO2014/036518
PCT Pub. Date: Mar. 6, 2014

(65) Prior Publication Data
US 2015/0233942 A1 Aug. 20, 2015

Related U.S. Application Data

(60) Provisional application No. 61/695,665, filed on Aug. 31, 2012.

(51) Int. Cl.
*G01N 33/68* (2006.01)
*G01N 33/74* (2006.01)

(52) U.S. Cl.
CPC ..... *G01N 33/6869* (2013.01); *G01N 33/6893* (2013.01); *G01N 33/74* (2013.01); *G01N 2333/585* (2013.01); *G01N 2800/26* (2013.01); *G01N 2800/7095* (2013.01)

(58) Field of Classification Search
None
See application file for complete search history.

(56) References Cited

U.S. PATENT DOCUMENTS

2009/0297474 A1* 12/2009 Kelleher ............... C12Q 1/6883
424/85.4

OTHER PUBLICATIONS

Simon et al, Clinical Infectious Diseases; 2004; vol. 39; pp. 206-217.*
Jafarzadeh et al, Cytokine, 2011, vol. 56, pp. 153-156.*
Yoshizaki et al, Annals of the Rheumatic Diseases, 2011; vol. 70, pp. 194-200.*
Hartmann, Analytical and Bioanalytical Chemistry; 2009; vol. 393; pp. 1407-1416.*
Wirtz et al, The Journal of Experimental Medicine, 2006; vol. 203, (8), pp. 1875-1881.*
Xu et al, Journal of Clinical Immunology; 2013; vol. 33, pp. 1257-1268.*
Burke et al, Critical Care Clinics, 2008; vol. 24, No. 2, pp. 313-334.*
Wong et al, Critical Care Oct. 29, 2012, pp. 1-8.*
Mokart et al, British Journal of Anesthesia, 2005, vol. 94, No. 6, pp. 767-773.*
Morgan et al, (Clinical Immunology; 2004, vol. 110, pp. 252-266.*
Basu et al. "Identification of Candidate Serum Biomarkers for Severe Septic Shock-Associated Kidney Injury via Microarray." *Crit. Care*. 15.6(2011):R273.
Cvijanovich et al. "Validating the Genomic Signature of Pediatric Septic Shock." *Physiol. Genomics*. 34.1(2008):127-134.
Eichler et al. "Gene Expression Dynamics Inspector (GEDI): For Integrative Analysis of Expression Profiles." *Bioinformatics*. 19.17(2003):2321-2322.
Goldstein et al. "International Pediatric Sepsis Consensus Conference: Definitions for Sepsis and Organ Dysfunction in Pediatrics." *Pediatr. Crit. Care Med*. 6.1(2005):2-8.
Guo et al. "Towards a Holistic, yet Gene-Centered Analysis of Gene Expression Profiles: A Case Study of Human Lung Cancers." *J. Biomed. Biotechnol*. 2006.5(2006):69141.
Irizarry et al. "Exploration, Normalization, and Summaries of High Density Oligonucleotide Array Probe Level Data." *Biostatistics*. 4.2(2003):249-264.
Lee et al. "Classification of Multiple Cancer Types by Multicategory Support Vector Machines Using Gene Expression Data." *Bioinformatics*. 19.9(2003):1132-1139.
Marshall et al. "Biomarkers of Sepsis." *Crit. Care Med*. 37.7(2009):2290-2298.
Muller et al. "Logistic Regression and CART in the Analysis of Multimarker Studies." *Clin. Chim. Acta*. 394(2008):1-6.
Nowak et al. "Admission Chemokine (C-C Motif) Ligand 4 Levels Predict Survival in Pediatric Septic Shock." *Pediatr. Crit. Care Med*. 11.2(2010):213-216.
Pflanz et al. "IL-27, a Heterodimeric Cytokine Composed of EB13 and p28 Protein, Induces Proliferation of Naïve CD4+ T Cells." *Immunity*. 16.6(2002):779-790.
Shanley et al. "Genome-Level Longitudinal Expression of Signaling Pathways and Gene Networks in Pediatric Septic Shock." *Mol. Med*. 13(2007):495-508.
Solan et al. "A Novel Role for Matrix Metalloproteinase-8 in Sepsis." *Crit. Care Med*. 40.2(2012):379-387.
Sutherland et al. "Development and Validation of a Novel Molecular Biomarker Diagnostic Test for the Early Detection of Sepsis." *Crit. Care*. 15.3(2011): R149.

(Continued)

Primary Examiner — Joanne Hama
Assistant Examiner — Fozia Hamud
(74) Attorney, Agent, or Firm — Mintz Levin Cohn Ferris Glovsky and Popeo, P.C.; Muriel Liberto, Esq.

(57) ABSTRACT

Embodiments of the invention are directed to methods of diagnosing bacterial infection in a critically ill patient. The methods include obtaining a sample from the patient and determining the patient's level of IL-27 expression. Embodiments of the invention are also directed to methods that include determining both the patient's levels of IL-27 expression and PCT expression and using the combined result to provide a diagnosis of bacterial infection in a critically ill patient.

15 Claims, 2 Drawing Sheets

(56) References Cited

OTHER PUBLICATIONS

Tang et al. "Accuracy of Procalcitonin for Sepsis Diagnosis in Critically Ill Patients: Systematic Review and Meta-Analysis." *Lancet Infect. Dis.* 7.3(2007):210-217.

Tang et al. "The Use of Gene-Expression Profiling to Identify Candiate Genes in Human Sepsis." *Am. J. Respir. Crit. Care Med.* 176.7(2007):676-684.

Villarino et al. "Positive and Negative Regulation of the IL-27 Receptor During Lymphoid Cell Activation." *J. Immunol.* 174.12(2005):7684-7691.

Wirtz et al. "Protection from Lethal Septic Peritonitis by Neutralizing the Biological Function of Interleukin 27." *J. Exp. Med.* 203.8(2006):1875-1881.

Wojno et al. "New Directions in the Basic and Translational Biology of Interleukin-27." *Trends Immunol.* 33.2(2012):91-97.

Wong et al. "Genome-Level Expression Profiles in Pediatric Septic Shock Indicate a Role for Altered Zinc Homeostasis in Poor Outcome." *Physiol. Genomics.* 30.2(2007):146-155.

Wong et al. "Genomic Expression Profiling Across the Pediatric Systemic Inflammatory Response Syndrome, Sepsis, and Septic Shock Spectrum." *Crit. Care Med.* 37.5(2009):1558-1566.

Wong et al. "Identification of Pediatric Septic Shock Subclasses Based on Genome-Wide Expression Profiling." *BMC Med.* 7(2009):34.

Wong et al. "Interleukin-8 as Stratficiation Tool for Interventional Trials Involving Pediatric Septic Shock." *Am. J. Respir. Crit. Care Med.* 178.3(2008):276-282.

Wong et al. "Leukocyte Subset-Derived Genomewide Expression Profiles in Pediatric Septic Shock." *Pediatr. Crit. Care Med.* 11.3(2010):349-355.

Wong et al. "Toward a Clinically Feasible Gene Expression-Based Subclassification Strategy for Septic Shock: Proof of Concept." *Crit. Care Med.* 38.10(2010):1955-1961.

Wong et al. "Validation of a Gene Expression-Based Subclassification Strategy for Pediatric Septic Shock." *Crit. Care Med.* 39.141(2011):2511-2517.

Wong. "Clinical Review: Sepsis and Septic Shock—The Potential of Gene Arrays." *Crit. Care.* 16.1(2012):204.

Wong. "Genetics and Genomics in Pediatric Septic Shock." *Crit. Care Med.* 40.5(2012):1618-1620.

Wynn et al. "The Influence of Developmental Age on the Early Transcriptomic Response of Children with Septic Shock." *Mol. Med.* 17(2011):1146-1156.

* cited by examiner

USE OF INTERLEUKIN-27 AS A DIAGNOSTIC BIOMARKER FOR BACTERIAL INFECTION IN CRITICALLY ILL PATIENTS

CROSS-REFERENCE TO RELATED APPLICATION

This application claims the benefit of U.S. Provisional Patent Application No. 61/695,665, filed on Aug. 31, 2012, and is the U.S. national phase of PCT International Application Number PCT/US2013/057711, filed Aug. 30, 2013, the contents of which are incorporated by reference in their entirety.

STATEMENT REGARDING FEDERALLY-SPONSORED RESEARCH

This invention was made with government support under GM064619 and HL100474 awarded by the National Institutes of Health. The government has certain rights in the invention.

FIELD OF THE INVENTION

The invention disclosed herein generally relates to biomarkers associated with bacterial infection.

BACKGROUND

Systemic Inflammatory Response Syndrome (SIRS) is a condition associated with a systemic inflammatory response to an infection. SIRS can occur in patients with sterile inflammation processes (for example, pancreatitis, multiple trauma, ischemia, etc.) or with bacterial infections. SIRS is commonly diagnosed when two or more of the following symptoms are present: body temperature less than 36° C. or greater than 38° C., heart rate greater than 90 beats per minute, respiratory rate of more than 20 breaths per minute or atrial carbon dioxide tension of less than 32 mm Hg, and a white blood cell count of greater than 12,000 µL or less than 4,000/µL or 10% immature forms. Sepsis is a subtype of SIRS and is commonly diagnosed when a patient has SIRS in combination with a bacterial infection. Septic shock is a condition that results from uncontrolled sepsis and is commonly diagnosed when a sepsis patient develops refractory hypotension. In order to properly treat the patient, it is important to differentiate between critically ill patients with sterile inflammation and critically ill patients with a bacterial infection. As a general example, antibiotics would not be beneficial to patients with sterile inflammation (SIRS), but may benefit patients with bacterial infection (sepsis/septic shock).

Differentiating between sterile inflammation and bacterial infection in critically ill patients with fever and other signs of the systemic inflammatory response syndrome (SIRS) is an important clinical challenge (Tang, et al. *The Lancet Infectious Diseases* 7:210-7 (2007); Sutherland, et al. *Crit. Care* 15:R149 (2011); Tang, et al. *Am. J. Resp. Crit. Care Med.* 176:676-84 (2007)). While conventional microbiology culture techniques are the standard methodology for such differentiation, these techniques can lack sensitivity. In addition, there is often a substantial delay between obtaining cultures and generating clinically useful data.

SUMMARY

Embodiments of the invention provide methods for differentiating between sterile inflammation and bacterial infection in critically ill patients with fever and other signs of the systemic inflammatory response syndrome (SIRS) with high specificity and a high positive predictive value. The methods can include obtaining a serum sample from a critically ill patient (meeting criteria for SIRS or sepsis); measuring serum IL-27 protein concentration in the sample; and treating the patient for bacterial infection where the serum IL-27 protein concentration is 5 ng/ml or higher.

In some embodiments, the IL-27 protein concentration of 5 ng/ml or higher can provide a diagnosis of bacterial infection in a critically ill patient with greater than 80% specificity and/or greater than 80% positive predictive value; in some embodiments, the IL-27 protein concentration of 5 ng/ml or higher can provide a diagnosis of bacterial infection in a critically ill patient with greater than 90% specificity and/or greater than 90% positive predictive value. In some embodiments, the measuring can be done within 24 hours of the patient meeting criteria for SIRS or sepsis. In some embodiments of the invention, PCT concentration can also be measured, and the IL-27 and the PCT protein concentration results can be used in combination to differentiate sterile inflammation and bacterial infection in the patient.

Some embodiments provide methods for differentiating between sterile inflammation and bacterial infection in critically ill patients with fever and other signs of the systemic inflammatory response syndrome (SIRS) with high specificity and a high positive predictive value, comprising: obtaining a serum sample from a critically ill patient (meeting criteria for SIRS or sepsis); measuring serum IL-27 protein concentration in the sample; treating the patient for bacterial infection if a serum IL-27 protein concentration is 5 ng/ml or higher; measuring serum PCT concentration in the sample if a serum IL-27 protein concentration is less than 5 ng/ml; and treating the patient for sterile inflammation if the PCT concentration is less than 3 ng/ml. In some embodiments, the IL-27 protein concentration of 5 ng/ml or higher can provide a diagnosis of bacterial infection in a critically ill patient with greater than 80% specificity and/or greater than 80% positive predictive value; in some embodiments, an IL-27 protein concentration of 5 ng/ml or higher can provide a diagnosis of bacterial infection in a critically ill patient with greater than 90% specificity and/or greater than 90% positive predictive value. Likewise, in some embodiments, a PCT concentration of less than 3 ng/ml can provide a diagnosis of sterile inflammation in a critically ill patient with greater than 80% specificity and/or greater than 80% positive predictive value.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
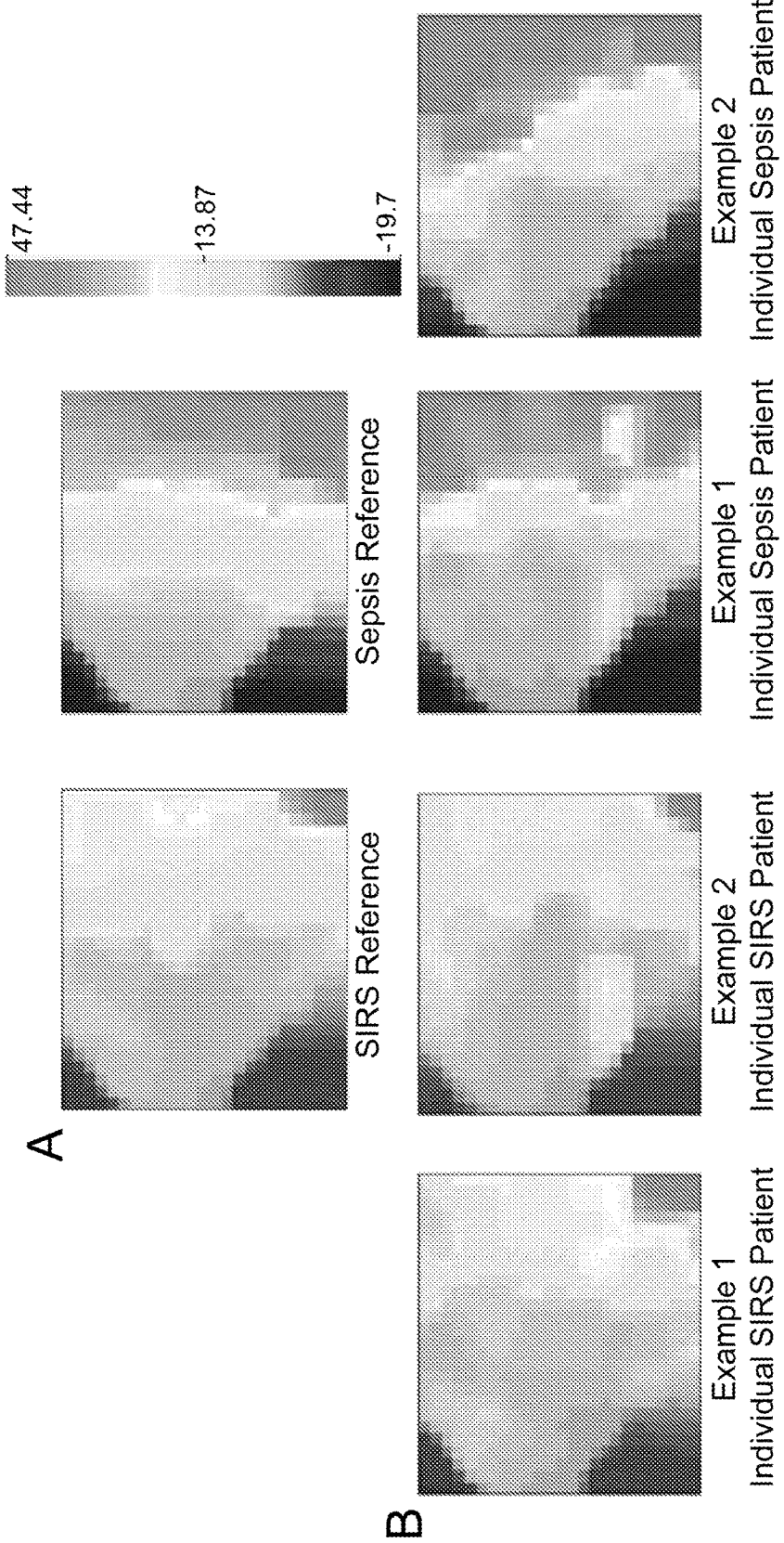
FIG. 1A depicts GEDI-generated reference mosaics for SIRS and sepsis classes. Each reference mosaic represents the average expression patterns of the top 100 class predictor genes (Table 2) for SIRS and sepsis classes, respectively.
FIG. 1B depicts examples of gene expression mosaics for individual patients. Each example depicts the same top 100 class predictor genes.

Unless otherwise noted, terms are to be understood according to conventional usage by those of ordinary skill in the relevant art.

As used herein, the term "sample" encompasses a sample obtained from a subject or patient. The sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, liquor cerebrospinalis, tear fluid, or cells therefrom. Samples can also include sections of tissues such as frozen or fixed sections taken for histological purposes or microdissected cells or extracellular parts thereof. A sample to be analyzed can be tissue material from an esophageal tissue biopsy obtained by aspiration or punctuation, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, "blood" can include, for example, plasma, serum, whole blood, blood lysates, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "diagnosing or monitoring" with reference to bacterial infection refers to a method or process of determining if a subject has or does not have bacterial infection or determining the severity or degree of bacterial infection.

As used herein, the term "modulated" or "modulation," or "regulated" or "regulation" and "differentially regulated" refers to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term "subject" refers to any member of the animal kingdom. In some embodiments, a subject is a human patient.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition.

As used herein, the term "transcriptomics" refers to the study of a disease "transcriptome," which is the set of all messenger RNA (mRNA) molecules, or "transcripts," produced in one or a population of cells. This term can also include non-translated RNAs which affect cellular characteristics because of gene regulation functions (silencing or activation or stabilization or degradation of other genes and transcripts). The term can be applied to the total set of transcripts in a given organism, or to the specific subset of transcripts present in a particular cell type. Unlike the genome, which is roughly fixed for a given cell line (excluding mutations), the transcriptome can vary with external environmental conditions. Because it includes all RNA transcripts in the cell, the transcriptome reflects the genes that are being actively expressed at any given time, with the exception of mRNA degradation phenomena such as transcriptional attenuation. It also includes posttranscriptional events such as alternative splicing.

As used herein, the term "expression levels" refers, for example, to a determined level of gene expression. The term "pattern of expression levels" refers to a determined level of gene expression compared either to a reference gene (e.g. a housekeeping gene or inversely regulated genes) or to a computed average expression value (e.g. in DNA-chip analyses). A pattern is not limited to the comparison of two genes but is more related to multiple comparisons of genes to reference genes or samples. A certain "pattern of expression levels" can also result and be determined by comparison and measurement of several genes as disclosed herein and display the relative abundance of these transcripts to each other.

As used herein, a "reference pattern of expression levels" refers to any pattern of expression levels that can be used for the comparison to another pattern of expression levels. In some embodiments of the invention, a reference pattern of expression levels is, for example, an average pattern of expression levels observed in a group of healthy or diseased individuals, serving as a reference group.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

Standard microbiology culture techniques have a number of technical and temporal limitations which prohibit effective and timely differentiation between sterile inflammation and bacterial infection in critically ill patients with fever and other signs of the systemic inflammatory response syndrome (SIRS). Biomarkers to differentiate sepsis from non-infectious causes of SIRS before microbiology data become available would be advantageous (Marshall, et al. *Crit. Care Med.* 37:2290-8 (2009)).

As described herein, an existing genome-wide expression database was mined for the discovery of candidate diagnostic biomarkers to predict the presence of bacterial infection in critically ill children. The data presented herein utilized a large genome-wide expression database (transcriptomics) of critically ill children with SIRS, sepsis, and septic shock by way of microarray technology (Wong *Crit. Care Med.* 40:1618-26 (2012); Wong *Crit. Care* 16:204 (2012); Basu, et al. *Crit. Care* 15:R273 (2011); Solan, et al. *Crit. Care Med.* 40:379-87 (2012); Wynn, et al. *Mol. Med.* 17:1146-56 (2011); Wong, et al. *Crit. Care Med.* 39:2511-7 (2011); Wong, et al. *Crit. Care Med.* 38:1955-61 (2010); Wong, et al. *Ped. Crit. Care Med.* 11:349-55 (2010); Wong, et al. *BMC Med.* 7:34 (2009); Wong, et al. *Crit. Care Med.* 37:1558-66 (2009); Wong, et al. *Am. J. Resp. Crit. Care Med.* 178:276-82 (2008); Cvijanovich, et al. *Physiol. Genom.* 34:127-34 (2008); Shanley, et al. *Mol. Med.* 13:495-508 (2007); Wong, et al. *Physiol. Genom.* 30:146-55 (2007)). These data were mined to discover gene signatures with the potential to differentiate sepsis from non-infectious causes of SIRS.

As described herein, a list of genes differentially regulated between critically ill patients with SIRS and critically ill patients with sepsis was generated by leveraging the discovery potential of microarray-based transcriptomics. This gene list represents a working list of candidate diagnostic biomarkers for bacterial infection in critically ill patients.

Genome-wide expression data were compared between patients with SIRS having negative bacterial cultures (n=21) and patients with sepsis having positive bacterial cultures (n=60). There were 221 gene probes differentially regulated between patients with SIRS and patients with sepsis. Differentially expressed genes were subjected to a leave-one-out cross validation (LOOCV) procedure to predict "SIRS" or "sepsis" classes. All data represented the first 24 hours of meeting criteria for either SIRS or sepsis.

The global expression patterns of the top 100 class predictor genes (Table 2) were able to predict "SIRS" and "sepsis" classes with high specificity and a high positive predictive value. The LOOCV procedure correctly predicted 86% of the SIRS and sepsis classes, and Epstein-Barr virus induced gene 3 (EBI3) had the highest predictive strength. Computer-assisted image analyses of gene expression mosaics were able to predict infection with a specificity of 90% and a positive predictive value of 94%.

Generating gene expression data and gene expression mosaics for 100 genes is not clinically feasible within the time-sensitive constraints of the intensive care unit. As EBI3, a subunit of the heterodimeric cytokine interleukin-27 (IL-27), had the highest predictive strength for bacterial infection of all the genes differentially regulated between patients with SIRS and patients with sepsis, the ability of serum IL-27 protein concentrations to predict bacterial infection in critically ill patients was determined. As procalcitonin (PCT) is currently being used clinically as a biomarker for bacterial infection in critically ill patients, serum concentrations of IL-27 and PCT were then compared between 101 patients with SIRS and 130 patients with sepsis.

IL-27 is a heterodimeric cytokine belonging to the IL-6 and IL-12 family of cytokines and is composed of the IL-27-p28 and EBI3 subunits, which are produced by antigen presenting cells upon exposure to microbial products (Wojno, et al. *Trends in Immunology* 33:91-7 (2012)). IL-27 is a T-cell regulator, having both pro- and anti-inflammatory effects (Pflanz, et al. *Immunity* 16:779-90 (2002); Villarino, et al. *J. Immunol.* 174:7684-91 (2005)). Furthermore, genetic ablation of EBI3 or neutralization of IL-27 via a soluble IL-27 receptor fusion protein is protective in a murine model of septic peritonitis (Wirtz, et al. *J. Exp. Med.* 203:1875-81 (2006)). Accordingly, it is biologically plausible that IL-27 can serve as a biomarker of bacterial infection in critically ill patients.

Embodiments of the invention are directed to methods for determining whether a critically ill patient has a bacterial infection. As described herein, at a cut-off point value of ≥5 ng/ml, serum IL-27 protein concentrations predicted infection with a specificity and a positive predictive value of >90%, and the overall performance of IL-27 was generally better than that of PCT. A decision tree combining IL-27 and PCT improved overall predictive capacity compared to either biomarker alone.

As described herein, through the genome-wide expression analysis, IL-27 has been found to represent a heretofore unknown diagnostic biomarker for predicting bacterial infection in critically ill patients. In addition, a combination of IL-27 and PCT improves the ability to predict infection, compared to that of either biomarker alone. Accordingly, embodiments of the invention also include methods for determining whether a critically ill patient has a bacterial infection by determining the patient's IL-27 expression or by combining the results from the patient's IL-27 expression with results from a determination of the patient's PCT expression. Such determinations can be taken alone or can be used with a reference pattern of expression.

Certain embodiments of the invention include using quantification data from a gene-expression analysis and/or from an mRNA analysis, from a sample of blood, urine, saliva, or the like. Embodiments of the invention include not only methods of conducting and interpreting such tests but also include reagents, kits, assays, and the like, for conducting the tests.

In an exemplary embodiment, the diagnostic method is carried out on a patient to determine if a critically ill patient has a bacterial infection. A serum sample is obtained from a critically ill patient. Serum IL-27 protein concentration is then measured (e.g. using a magnetic bead multi-plex platform and a Luminex® 100/200 System). The IL-27 result is then used in order to establish a diagnosis of bacterial infection. In another exemplary embodiment, both serum IL-27 protein concentration and PCT protein concentration are measured (e.g. using a magnetic bead multi-plex platform and a Luminex® 100/200 System). The IL-27 and PCT protein concentration results are then used in combination in order to establish a diagnosis of bacterial infection. Use of the decision tree depicted in FIG. 2 in order to determine the presence or absence of infection is another exemplary embodiment of the invention.

In some embodiments of the invention, a serum IL-27 protein concentration that is indicative of bacterial infection in a critically ill patient is 5 ng/ml or higher. In some embodiments of the invention, a serum IL-27 protein concentration that is indicative of bacterial infection in a critically ill patient is 5.1, 5.2, 5.3, 5.4, 5.5, 5.6, 5.7, 5.8, 5.9, or 6.0 ng/ml, or higher. In some embodiments of the invention, a serum IL-27 protein concentration that is indicative of bacterial infection in a critically ill patient is 4.1, 4.2, 4.3, 4.4, 4.5, 4.6, 4.7, 4.8, 4.9 or 5.0 ng/ml, or higher. In some embodiments of the invention, a serum IL-27 protein concentration that is indicative of bacterial infection in a critically ill patient is 3.1, 3.2, 3.3, 3.4, 3.5, 3.6, 3.7, 3.8, 3.9, or 4.0 ng/ml, or higher. In some embodiments of the invention, a serum IL-27 protein concentration that is indicative of bacterial infection in a critically ill patient is 2.1, 2.2, 2.3, 2.4, 2.5, 2.6, 2.7, 2.8, 2.9, or 3.0 ng/ml, or higher. In some embodiments of the invention, a serum IL-27 protein concentration that is indicative of bacterial infection in a critically ill patient is 1.0, 1.1, 1.2, 1.3, 1.4, 1.5, 1.6, 1.7, 1.8, 1.9, or 2.0 ng/ml, or higher. In some embodiments of the invention, a serum IL-27 protein concentration that is indicative of bacterial infection in a critically ill patient is less than 1.0 ng/ml.

In some embodiments of the invention, a combination of a serum IL-27 protein concentration and a serum PCT protein concentration that is indicative of bacterial infection in a critically ill patient is an IL-27 concentration of 5 ng/ml or high and a PCT concentration of 3 ng/ml. In some embodiments of the invention, a serum PCT protein concentration is used in combination with a serum IL-27 protein concentration that is 5.1, 5.2, 5.3, 5.4, 5.5, 5.6, 5.7, 5.8, 5.9, or 6.0 ng/ml, or higher, in order to diagnose bacterial infection in a critically ill patient. In some embodiments of the invention, a serum PCT protein concentration is used in combination with a serum IL-27 protein concentration that is 4.1, 4.2, 4.3, 4.4, 4.5, 4.6, 4.7, 4.8, 4.9, or 5.0 ng/ml, or higher, in order to diagnose bacterial infection in a critically ill patient. In some embodiments of the invention, a serum PCT protein concentration is used in combination with a serum IL-27 protein concentration that is 3.1, 3.2, 3.3, 3.4, 3.5, 3.6, 3.7, 3.8, 3.9, or 4.0 ng/ml, or higher, in order to diagnose bacterial infection in a critically ill patient. In some embodiments of the invention, a serum PCT protein concentration is used in combination with a serum IL-27 protein concentration that is 2.1, 2.2, 2.3, 2.4, 2.5, 2.6, 2.7, 2.8, 2.9, or 3.0 ng/ml, or higher, in order to diagnose bacterial infection in a critically ill patient. In some embodiments of the invention, a serum PCT protein concentration is used in combination with a serum IL-27 protein concentration that is 1.0, 1.1, 1.2, 1.3, 1.4, 1.5, 1.6, 1.7, 1.8, 1.9, or 2.0 ng/ml, or higher, in order to diagnose bacterial infection in a critically ill patient. In some embodiments of the invention, a serum PCT protein concentration is used in combination with a serum IL-27 protein concentration that is less than 1.0 ng/ml, in order to diagnose bacterial infection in a critically ill patient. In some embodiments of the invention, a serum IL-27 protein concentration is used in combination with a serum PCT protein concentration that is 3.1, 3.2, 3.3, 3.4, 3.5, 3.6, 3.7, 3.8, 3.9, or 4.0 ng/ml, or higher, in order to diagnose bacterial infection in a critically ill patient. In some embodiments of the invention, a serum IL-27 protein concentration is used in combination with a serum PCT protein concentration that is 2.1, 2.2, 2.3, 2.4, 2.5, 2.6, 2.7, 2.8, 2.9, or 3.0 ng/ml, or higher, in order to diagnose bacterial infection in a critically ill patient. In some embodiments of the invention, a serum IL-27 protein concentration is used in combination with a serum PCT protein concentration that is 1.1, 1.2, 1.3, 1.4, 1.5, 1.6, 1.7, 1.8, 1.9, or 2.0 ng/ml, or higher, in order to diagnose bacterial infection in a critically ill patient. In some embodiments of the invention, a serum IL-27 protein concentration is used in combination with a serum PCT protein concentration that is 0.5, 0.6, 0.7, 0.8, 0.9, or 1.0 ng/ml, or higher, in order to diagnose bacterial infection in a critically ill patient. In some embodiments of the invention, a serum IL-27 protein concentration is used in combination with a serum PCT protein concentration that is less than 0.5 ng/ml, in order to diagnose bacterial infection in a critically ill patient.

Embodiments of the invention also encompass methods of providing individualized treatment for a critically ill patient with SIRS, wherein a patient classified as having sterile inflammation via the methods described herein can be selected for one of more SIRS therapies, and wherein a patient classified as having SIRS with a bacterial infection via the methods described herein can be selected for one or more sepsis therapies. In some embodiments, SIRS therapies include intubation, supplemental oxygen, assisted ventilation, fluid and electrolyte resuscitation, surgical procedures, kidney dialysis, blood pressure medication, and the like. Examples of surgical procedures may include drainage of abscesses or drainable foci of infection. In some embodiments, sepsis therapies include one or more SIRS therapies in combination with appropriate antibiotics. Examples of appropriate antibiotics may include cefotaxime, ticarcillin-clavulanate, piperacillin-tazobactam, imipenem-cilastatin, meropenem, clindamycin, metronidazole, ceftriaxone, ciprofloxacin, cefepime, levofloxacin, and vanomycin.

Diagnostic-testing procedure performance is commonly described by evaluating control groups to obtain four critical test characteristics, namely positive predictive value (PPV), negative predictive value (NPV), sensitivity, and specificity, which provide information regarding the effectiveness of the test. The PPV of a particular diagnostic test represents the proportion of subjects with a positive test result who are correctly diagnosed; for tests with a high PPV, a positive test indicates the presence of the condition in question. The NPV of a particular diagnostic test represents the proportion of subjects with a negative test result who are correctly diagnosed; for tests with a high NPV, a negative test indicates the absence of the condition. Sensitivity represents the proportion of correctly identified subjects who are actual positives; for tests with high sensitivity, a positive test indicates the presence of the condition in question. Specificity represents the proportion of correctly identified subjects who are actual negatives; for tests with high specificity, a negative test indicates the absence of the condition.

The threshold for the disease state can alternatively be defined as a 1-D quantitative score, or diagnostic cutoff, based upon receiver operating characteristic (ROC) analysis. The quantitative score based upon ROC analysis can be used to determine the specificity and/or the sensitivity of a given diagnostic cutoff, or serum IL-27 protein concentration that is indicative of bacterial infection in a critically ill patient. In some embodiments, the diagnostic cut-off is 5 ng/ml.

In some embodiments, the quantitative score based upon ROC analysis is one that provides a diagnosis of bacterial infection in a critically ill patient with greater than 90% specificity and greater than 90% positive predictive value. In some embodiments, the quantitative score based upon ROC analysis is one that provides a diagnosis of bacterial infection in a critically ill patient with greater than 80% specificity and greater than 80% positive predictive value.

In some embodiments, the quantitative score based upon ROC analysis is one that provides a diagnosis of bacterial infection in a critically ill patient with greater than 90% specificity or greater than 90% positive predictive value. In some embodiments, the quantitative score based upon ROC analysis is one that provides a diagnosis of bacterial infection in a critically ill patient with greater than 80% specificity or greater than 80% positive predictive value.

In some embodiments, the quantitative score based upon ROC analysis is one that provides a diagnosis of bacterial infection in a critically ill patient with greater than 80%, 81%, 82%, 83%, 84%, 85%, 86%, 87%, 88%, or 89% specificity. In some embodiments, the quantitative score based upon ROC analysis is one that provides a diagnosis of bacterial infection in a critically ill patient with greater than 90%, 91%, 92%, 93%, 94%, 95%, 96%, 97%, 98%, or 99% specificity. In some embodiments, the quantitative score based upon ROC analysis is one that provides a diagnosis of bacterial infection in a critically ill patient with a specificity of higher than 99%.

In some embodiments, the quantitative score based upon ROC analysis is one that provides a diagnosis of bacterial infection in a critically ill patient with greater than 80%, 81%, 82%, 83%, 84%, 85%, 86%, 87%, 88%, or 89% positive predictive value. In some embodiments, the quantitative score based upon ROC analysis is one that provides a diagnosis of bacterial infection in a critically ill patient with greater than 90%, 91%, 92%, 93%, 94%, 95%, 96%, 97%, 98%, or 99% positive predictive value. In some embodiments, the quantitative score based upon ROC analysis is one that provides a diagnosis of bacterial infection in a critically ill patient with a positive predictive value of higher than 99%.

In some embodiments, the quantitative score based upon ROC analysis is one that provides a diagnosis of bacterial infection in a critically ill patient with greater than 80% specificity and greater than 80% positive predictive value. In some embodiments, the quantitative score based upon ROC analysis is one that provides a diagnosis of bacterial infection in a critically ill patient with greater than 81% specificity and greater than 81% positive predictive value. In some embodiments, the quantitative score based upon ROC analysis is one that provides a diagnosis of bacterial infection in a critically ill patient with greater than 82% specificity and greater than 82% positive predictive value. In some embodiments, the quantitative score based upon ROC analysis is one that provides a diagnosis of bacterial infection in a critically ill patient with greater than 83% specificity and greater than 83% positive predictive value. In some embodiments, the quantitative score based upon ROC analysis is one that provides a diagnosis of bacterial infection in a critically ill patient with greater than 84% specificity and greater than 84% positive predictive value. In some embodiments, the quantitative score based upon ROC analysis is one that provides a diagnosis of bacterial infection in a critically ill patient with greater than 85% specificity and greater than 85% positive predictive value. In some embodiments, the quantitative score based upon ROC analysis is one that provides a diagnosis of bacterial infection in a critically ill patient with greater than 86% specificity and greater than 86% positive predictive value. In some embodiments, the quantitative score based upon ROC analysis is one that provides a diagnosis of bacterial infection in a critically ill patient with greater than 87% specificity and greater than 87% positive predictive value. In some embodiments, the quantitative score based upon ROC analysis is one that provides a diagnosis of bacterial infection in a critically ill patient with greater than 88% specificity and greater than 88% positive predictive value. In some embodiments, the quantitative score based upon ROC analysis is one that provides a diagnosis of bacterial infection in a critically ill patient with greater than 89% specificity and greater than 89% positive predictive value.

In some embodiments, the quantitative score based upon ROC analysis is one that provides a diagnosis of bacterial infection in a critically ill patient with greater than 90% specificity and greater than 90% positive predictive value. In some embodiments, the quantitative score based upon ROC analysis is one that provides a diagnosis of bacterial infection in a critically ill patient with greater than 91% specificity and greater than 91% positive predictive value. In some embodiments, the quantitative score based upon ROC analysis is one that provides a diagnosis of bacterial infection in a critically ill patient with greater than 92% specificity and greater than 92% positive predictive value. In some embodiments, the quantitative score based upon ROC analysis is one that provides a diagnosis of bacterial infection in a critically ill patient with greater than 93% specificity and greater than 93% positive predictive value. In some embodiments, the quantitative score based upon ROC analysis is one that provides a diagnosis of bacterial infection in a critically ill patient with greater than 94% specificity and greater than 94% positive predictive value. In some embodiments, the quantitative score based upon ROC analysis is one that provides a diagnosis of bacterial infection in a critically ill patient with greater than 95% specificity and greater than 95% positive predictive value.

In some embodiments, the quantitative score based upon ROC analysis is one that provides a diagnosis of bacterial infection in a critically ill patient with greater than 80%, 81%, 82%, 83%, 84%, 85%, 86%, 87%, 88%, or 89% sensitivity. In some embodiments, the quantitative score based upon ROC analysis is one that provides a diagnosis of bacterial infection in a critically ill patient with greater than 90%, 91%, 92%, 93%, 94%, 95%, 96%, 97%, 98%, or 99% sensitivity. In some embodiments, the quantitative score based upon ROC analysis is one that provides a diagnosis of bacterial infection in a critically ill patient with a sensitivity of higher than 99%.

The correlations disclosed herein, between septic shock biomarker levels and/or mRNA levels and/or gene expression levels, provide a basis for conducting a diagnosis of septic shock, or for conducting a stratification of patients with septic shock, or for enhancing the reliability of a diagnosis of septic shock by combining the results of a quantification of a septic shock biomarker with results from other tests or indicia of septic shock. For example, the results of a quantification of one biomarker could be combined with the results of a quantification of one or more additional biomarker, cytokine, mRNA, or the like. Thus, even in situations in which a given biomarker correlates only moderately or weakly with septic shock, providing only a relatively small PPV, NPV, specificity, and/or sensitivity, the correlation can be one indicium, combinable with one or more others that, in combination, provide an enhanced clarity and certainty of diagnosis. Accordingly, the methods and materials of the invention are expressly contemplated to be used both alone and in combination with other tests and indicia, whether quantitative or qualitative in nature.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Patients and Data Collection

Patient Cohort

The study described herein involved 17 participating institutions; the study protocol has been previously described in detail (Wong, et al. *Crit. Care Med.* 37:1558-66 (2009); Wong, et al. *Physiol. Genom.* 30:146-55 (2007)). Briefly, children ≤10 years of age admitted to the pediatric intensive care unit (PICU) and meeting pediatric-specific criteria for SIRS, sepsis, or septic shock were eligible for enrollment (Goldstein, et al. *Ped. Crit. Care Med.* 6:2-8 (2005)). After informed consent from parents or legal guardians, blood samples were obtained within 24 hours of initial presentation to the PICU with SIRS, sepsis, or septic shock. Clinical and laboratory data were collected daily while in the PICU and stored using a web-based database. Mortality was tracked for 28 days after enrollment, and organ failure data was based on pediatric-specific criteria (Goldstein, et al. *Ped. Crit. Care Med.* 6:2-8 (2005)).

All patients with microarray data in the current study were previously reported in studies addressing hypotheses entirely different from that of the current report (Basu, et al. *Crit. Care* 15:R273 (2011); Wynn, et al. *Mol. Med.* 17:1146-56 (2011); Wong, et al. *Crit. Care Med.* 39:2511-7 (2011); Wong, et al. *Crit. Care Med.* 38:1955-61 (2010); Wong, et al. *Ped. Crit. Care Med.* 11:349-55 (2010); Wong, et al. *BMC Med.* 7:34 (2009); Wong, et al. *Crit. Care Med.* 37:1558-66 (2009); Wong, et al. *Am. J. Resp. Crit. Care Med.* 178:276-82 (2008); Cvijanovich, et al. *Physiol. Genom.* 34:127-34 (2008); Wong0, et al. *Physiol. Genom.* 30:146-55 (2007); Nowak, et al. *Ped. Crit. Care Med.* 11:213-6 (2010)). For the study described herein, all patients in the sepsis and septic shock cohorts had clinical microbiology laboratory confirmation of a bacterial pathogen from blood cultures or other normally sterile body fluids, whereas all patients in the SIRS cohort had negative bacterial cultures.

RNA Extraction, Microarray Hybridization, and Microarray Analysis

Total RNA was isolated from whole blood samples using the PAXGENE™ Blood RNA System (PreAnalytiX, Qiagen/Becton Dickson, Valencia, Calif.) according the manufacturer's specifications. Microarray hybridization was performed by the Affymetrix GeneChip Core facility at Cincinnati Children's Hospital Research Foundation, as previously described, using the HumanGenome U133 Plus 2.0 GeneChip (Affymetrix, Santa Clara, Calif.) (Wong, et al. *Physiol. Genom.* 30:146-55 (2007)).

Analyses were performed using one patient sample per chip. Image files were captured using an Affymetrix GeneChip Scanner 3000. Raw data files were subsequently preprocessed using Robust Multiple-array Average (RMA) normalization using GeneSpring GX 7.3 software (Agilent Technologies, Palo Alto, Calif.) (Irizarry, et al. *Biostatistics* 4:249-64 (2003)). All chips were then normalized to the respective median values of normal, age-matched controls, as previously described (Wong, et al. *Physiol. Genom.* 30:146-55 (2007)). Differences in mRNA abundance between patient samples were determined using GeneSpring GX 7.3. All statistical analyses used corrections for multiple comparisons.

Generation of Gene Expression Mosaics

Expression mosaics were generated using the Gene Expression Dynamics Inspector (GEDI) platform. GEDI is a publicly available gene expression analysis program developed by the Ingber Laboratory at Harvard University (Eichler, et al. *Bioinformatics* 19:2321-2 (2003); Guo, et al. *J. Biomed. Biotech.* 2006:69141 (2006)). The signature graphical outputs of GEDI are gene expression mosaics that give microarray data a "face" that is intuitively recognizable via human pattern recognition (Wong, et al. *Crit. Care Med.* 39:2511-7 (2011); Wong, et al. *Crit. Care Med.* 38:1955-61 (2010)). The underlying algorithm for creating the mosaics is a self-organizing map (SOM).

Computer-Assisted Image Analysis

Individual patient mosaics were compared to SIRS and sepsis reference mosaics using a publicly available image analysis platform (ImageJ, http <colon slash slash> rsbweb <dot> nih <dot> gov <slash> ij), as previously described (Wong, et al. *Crit. Care Med.* 39:2511-7 (2011)). Briefly, the absolute difference in RGB pixel-to-pixel intensity was calculated for each individual patient mosaic relative to the SIRS and sepsis reference mosaics. Final classification was based on the "least difference" between the individual patient mosaic and the two reference mosaics.

Measurement of IL-27 and Procalcitonin Serum Protein Concentrations

Serum IL-27 (EMD Millipore Corporation, Billerica, Mass.) and procalcitonin (Bio-Rad, Hercules, Calif.) protein concentrations were measured using a magnetic bead multiplex platform and a Luminex® 100/200 System (Luminex Corporation, Austin, Tex.), according the manufacturers' specifications.

Statistical Analysis

Initially, data were described using medians, interquartile ranges, and percents. Comparisons between study cohorts used the Mann-Whitney U-test, Chi-square, or Fisher's Exact tests as appropriate. Descriptive statistics and comparisons used SigmaStat Software (Systat Software, Inc., San Jose, Calif.). Classification and regression tree (CART) analysis was conducted using the Salford Predictive Modeler v6.6 (Salford Systems, San Diego, Calif.) (Muller, et al. *Clin. Chian. Acta* 394:1-6 (2008)). Biomarker test characteristics were reported using diagnostic test statistics with 95% confidence intervals computed using the score method as implemented by VassarStats Website for Statistical Computation (http <colon slash slash> faculty <dot> vasser <dot> edu <slash> lowry <slash> VasserStats <dot> html).

Example 2

Initial Identification of Candidate Sepsis Diagnostic Genes

Candidate sepsis diagnostic genes were identified using a convenience sample of existing patients in the genome-wide expression database of critically ill children meeting criteria for either SIRS with negative bacterial cultures (n=21) or sepsis with positive bacterial cultures (n=60). All gene expression data reflect the first 24 hours of meeting clinical criteria for SIRS or sepsis. Fifty-three of the patients with sepsis also met criteria for septic shock. The basic clinical and demographic characteristics of the SIRS and sepsis cohorts are shown in Table 1. Patients in the sepsis cohort were younger and had a higher pediatric risk of mortality (PRISM) score compared to patients in the SIRS cohort.

TABLE 1

Clinical characteristics of the gene expression cohort.

|  | SIRS (n = 21) | Sepsis (n = 60) |
|---|---|---|
| Median Age in Years | 3.3 (2.0-8.3) | 1.9 (0.6-5.1)* |
| Males (%) | 52 | 67 |
| Median PRISM Score | 10 (4-14) | 14 (10-21)* |
| Mortality (%) | 5 | 22 |

*$p < 0.05$ vs. SIRS

The initial step for identifying candidate sepsis diagnostic genes involved an expression filter. Starting with all gene probes on the array (>80,000), gene probes were selected as having ≥2-fold expression between the median values of patients with sepsis and patients with SIRS. This expression filter yielded 228 gene probes. The 228 gene probes were then subjected to a statistical test (analysis of variance (ANOVA) with a Benjamini-Hochberg false discovery rate of 5%) using the sepsis and SIRS cohorts as the comparison groups. This statistical test yielded 221 gene probes that were differentially regulated between patients with sepsis and patients with SIRS.

A leave-one-out cross validation (LOOCV) procedure was then performed to determine if the expression patterns of the 221 differentially regulated gene probes could identify "SIRS" and "sepsis" classes. LOOCV is a machine learning algorithm. The present case used the "Support Vector Machines" algorithm, which removes one of the patients ("patient A") and evaluates the expression patterns of the genes of interest in the remaining patients who are infected and the remaining patients who are not infected. Based on the analysis of these gene expression patterns, the algorithm predicts whether or not "patient A" is infected. It then puts patient A back into the patient pool, then removes another patient ("patient B") and runs the same process. This procedure is repeated until each patient in the cohort has been examined (Lee and Lee, Bioinformatics 19:1132-1139 (2003)).

The LOOCV procedure correctly predicted 86% of the SIRS or sepsis classes. The top one hundred class predictor genes (based on predictive strength) are provided in Table 2. Epstein-Barr virus-induced gene 3 (EBI3) was found to have the highest predictive strength.

TABLE 2

Top 100 class predictor genes.

| Affymetrix ID | Predictive Strength | Symbol | Description |
|---|---|---|---|
| 219424_at | 19.98 | EBI3 | Epstein-Barr virus induced gene 3 |
| 1570511_at | 17.84 | ARHGEF10L | Rho guanine nucleotide exchange factor (GEF) 10-like |
| 232382_s_at | 15.4 | PCMTD1 | protein-L-isoaspartate (D-aspartate) O-methyltransferase domain containing 1 |
| 238996_x_at | 15.34 | ALDOA | aldolase A, fructose-bisphosphate |
| 206370_at | 15.1 | PIK3CG | phosphoinositide-3-kinase, catalytic, gamma polypeptide |
| 230759_at | 15.1 | SNX14 | Sorting nexin 14 |
| 201123_s_at | 14.67 | EIF5A | eukaryotic translation initiation factor 5A |
| 219975_x_at | 14.67 | OLAH | oleoyl-ACP hydrolase |
| 208322_s_at | 14.49 | ST3GAL1 | ST3 beta-galactoside alpha-2,3-sialyltransferase 1 |
| 220232_at | 14.25 | SCD5 | stearoyl-CoA desaturase 5 |
| 205838_at | 13.73 | GYPA | glycophorin A (MNS blood group) |
| 202953_at | 13.38 | C1QB | complement component 1, q subcomponent, B chain |
| 219622_at | 13.38 | RAB20 | RAB20, member RAS oncogene family |
| 215838_at | 13.32 | LILRA5 | leukocyte immunoglobulin-like receptor, subfamily A (with TM domain), member 5 |
| 218737_at | 13.32 | SBNO1 | strawberry notch homolog 1 (Drosophila) |
| 200951_s_at | 13.28 | CCND2 | cyclin D2 |
| 236407_at | 12.92 | KCNE1 | potassium voltage-gated channel, Isk-related family, member 1 |
| 215856_at | 12.8 | SIGLEC15 | sialic acid binding Ig-like lectin 15 |
| 236033_at | 12.76 | ASB12 | ankyrin repeat and SOCS box-containing 12 |
| 208308_s_at | 12.25 | GPI | glucose phosphate isomerase |
| 238363_at | 12.22 | CAT | Catalase |
| 242428_at | 12.22 | DCUN1D1 | DCN1, defective in cullin neddylation 1, domain containing 1 (S. cerevisiae) |
| 213579_s_at | 12.22 | EP300 | E1A binding protein p300 |
| 231524_at | 12.22 | KCNAB1 | potassium voltage-gated channel, shaker-related subfamily, beta member 1 |
| 244774_at | 11.7 | PHACTR2 | phosphatase and actin regulator 2 |
| 203819_s_at | 11.69 | IGF2BP3 | insulin-like growth factor 2 mRNA binding protein 3 |
| 266_s_at | 11.17 | CD24 | CD24 molecule |
| 220017_x_at | 11.17 | CYP2C9 | cytochrome P450, family 2, subfamily C, polypeptide 9 |
| 211372_s_at | 10.92 | IL1R2 | interleukin 1 receptor, type II |
| 206420_at | 10.9 | IGSF6 | immunoglobulin superfamily, member 6 |
| 211565_at | 10.9 | SH3GL3 | SH3-domain GRB2-like 3 |
| 1552806_a_at | 10.84 | SIGLEC10 | sialic acid binding Ig-like lectin 10 |
| 1564164_at | 10.67 | DENND1B | DENN/MADD domain containing 1B |
| 232138_at | 10.67 | MBNL2 | Muscleblind-like 2 (Drosophila) |
| 202785_at | 10.67 | NDUFA7 | NADH dehydrogenase (ubiquinone) 1 alpha subcomplex, 7, 14.5 kDa |
| 202397_at | 10.67 | NUTF2 | nuclear transport factor 2 |
| 232392_at | 10.67 | SFRS3 | Splicing factor, arginine/serine-rich 3 |
| 209258_s_at | 10.67 | SMC3 | structural maintenance of chromosomes 3 |
| 213624_at | 10.59 | SMPDL3A | sphingomyelin phosphodiesterase, acid-like 3A |
| 216331_at | 10.31 | ITGA7 | integrin, alpha 7 |
| 201061_s_at | 10.27 | STOM | stomatin |

TABLE 2-continued

Top 100 class predictor genes.

| Affymetrix ID | Predictive Strength | Symbol | Description |
|---|---|---|---|
| 205040_at | 10.23 | ORM1 | orosomucoid 1 |
| 234701_at | 10.17 | ANKRD11 | ankyrin repeat domain 11 |
| 232063_x_at | 10.17 | FARSB | phenylalanyl-tRNA synthetase, beta subunit |
| 209267_s_at | 10.17 | SLC39A8 | solute carrier family 39 (zinc transporter), member 8 |
| 202071_at | 10.07 | SDC4 | syndecan 4 |
| 211883_x_at | 9.727 | CEACAM1 | carcinoembryonic antigen-related cell adhesion molecule 1 (biliary glycoprotein) |
| 244443_at | 9.693 | CHD2 | Chromodomain helicase DNA binding protein 2 |
| 230609_at | 9.693 | CLINT1 | clathrin interactor 1 |
| 1557749_at | 9.693 | EHBP1L1 | EH domain binding protein 1-like 1 |
| 235057_at | 9.693 | ITCH | itchy E3 ubiquitin protein ligase homolog (mouse) |
| 1556336_at | 9.693 | CCBL2 | cysteine conjugate-beta lyase 2 |
| 203435_s_at | 9.578 | MME | membrane metallo-endopeptidase |
| 226448_at | 9.568 | FAM89A | family with sequence similarity 89, member A |
| 1554241_at | 9.223 | COCH | coagulation factor C homolog, cochlin (*Limulus polyphemus*) |
| 206697_s_at | 9.223 | HP | haptoglobin |
| 207794_at | 9.171 | CCR2 | chemokine (C-C motif) receptor 2 |
| 205041_s_at | 8.949 | ORM1 | orosomucoid 1 |
| 226675_s_at | 8.763 | MALAT1 | metastasis associated lung adenocarcinoma transcript 1 (non-protein coding) |
| 237741_at | 8.763 | SLC25A36 | Solute carrier family 25, member 36 |
| 223796_at | 8.73 | CNTNAP3 | contactin associated protein-like 3 |
| 203949_at | 8.712 | MPO | myeloperoxidase |
| 225207_at | 8.537 | PDK4 | pyruvate dehydrogenase kinase, isozyme 4 |
| 209750_at | 8.407 | NR1D2 | nuclear receptor subfamily 1, group D, member 2 |
| 205513_at | 8.368 | TCN1 | transcobalamin I (vitamin B12 binding protein, R binder family) |
| 1555920_at | 8.314 | CBX3 | Chromobox homolog 3 (HP1 gamma homolog, *Drosophila*) |
| 231951_at | 8.314 | GNAO1 | guanine nucleotide binding protein (G protein), alpha activating activity polypeptide O |
| 204351_at | 8.244 | S100P | S100 calcium binding protein P |
| 202388_at | 8.123 | RGS2 | regulator of G-protein signaling 2, 24 kDa |
| 209906_at | 7.974 | C3AR1 | complement component 3a receptor 1 |
| 206177_s_at | 7.874 | ARG1 | arginase, liver |
| 36711_at | 7.874 | MAFF | v-maf musculoaponeurotic fibrosarcoma oncogene homolog F (avian) |
| 202742_s_at | 7.874 | PRKACB | protein kinase, cAMP-dependent, catalytic, beta |
| 212531_at | 7.774 | LCN2 | lipocalin 2 |
| 223767_at | 7.731 | GPR84 | G protein-coupled receptor 84 |
| 219607_s_at | 7.443 | MS4A4A | membrane-spanning 4-domains, subfamily A, member 4 |
| 212249_at | 7.443 | PIK3R1 | phosphoinositide-3-kinase, regulatory subunit 1 (alpha) |
| 212793_at | 7.323 | DAAM2 | dishevelled associated activator of morphogenesis 2 |
| 241981_at | 7.323 | FAM20A | family with sequence similarity 20, member A |
| 206676_at | 7.303 | CEACAM8 | carcinoembryonic antigen-related cell adhesion molecule 8 |
| 231235_at | 7.302 | NKTR | natural killer-tumor recognition sequence |
| 230972_at | 7.189 | ANKRD9 | ankyrin repeat domain 9 |
| 202018_s_at | 7.184 | LTF | lactotransferrin |
| 220646_s_at | 7.138 | KLRF1 | killer cell lectin-like receptor subfamily F, member 1 |
| 238439_at | 7.021 | ANKRD22 | ankyrin repeat domain 22 |
| 219669_at | 7.021 | CD177 | CD177 molecule |
| 205001_s_at | 7.021 | DDX3Y | DEAD (Asp-Glu-Ala-Asp) box polypeptide 3, Y-linked |
| 205557_at | 6.821 | BPI | bactericidal/permeability-increasing protein |
| 211734_s_at | 6.821 | FCER1A | Fc fragment of IgE, high affinity I, receptor for; alpha polypeptide |
| 222838_at | 6.821 | SLAMF7 | SLAM family member 7 |
| 1565358_at | 6.769 | RARA | retinoic acid receptor, alpha |
| 242918_at | 6.607 | NASP | Nuclear autoantigenic sperm protein (histone-binding) |
| 213906_at | 6.47 | MYBL1 | v-myb myeloblastosis viral oncogene homolog (avian)-like 1 |
| 205220_at | 6.363 | GPR109B | G protein-coupled receptor 109B |
| 220570_at | 6.152 | RETN | resistin |
| 204409_s_at | 6.067 | EIF1AY | eukaryotic translation initiation factor 1A, Y-linked |
| 223670_s_at | 5.969 | HEMGN | hemogen |
| 205033_s_at | 5.589 | DEFA1 | defensin, alpha 1 |
| 210356_x_at | 5.414 | MS4A1 | membrane-spanning 4-domains, subfamily A, member 1 |
| 231688_at | 5.031 | MMP8 | matrix metallopeptidase 8 (neutrophil collagenase) |

Example 3

Gene Expression Mosaics of the Top 100 Class Predictor Genes

The expression values of the top 100 class predictor genes were uploaded to the GEDI platform, and reference gene expression mosaics were generated for patients with SIRS and patients with sepsis, respectively (FIG. 1A). The reference mosaics represent the average expression patterns for all patients in each class and demonstrate distinct expression patterns for the patients with sepsis compared to the patients with SIRS. Examples of individual patient mosaics are provided in FIG. 1B.

To determine if the expression mosaics could correctly identify SIRS and sepsis classes, computer-assisted image analysis was performed. The image analysis algorithm compared individual patient mosaics to the two reference mosaics and assigned the individual patients to either SIRS or sepsis classes based on similarity of expression (Wong, et al. Crit. Care Med. 39:2511-7 (2011)). The test characteristics of this analysis are provided in Table 3.

TABLE 3

Test characteristics of gene expression mosaics for identifying sepsis versus SIRS.

|  | % | 95% Confidence Interval |
|---|---|---|
| Sensitivity | 53 | 39-66 |
| Specificity | 90 | 68-98 |
| Positive Predictive Value | 94 | 78-99 |
| Negative Predictive Value | 40 | 27-56 |

The expression mosaics were able to identify patients with infection (sepsis) with a high degree of specificity (90%) and a high positive predictive value (94%). Thus, the top 100 class predictor genes represent a working list of candidate diagnostic biomarkers for the presence of bacterial infection in critically ill patients.

Example 4

IL-27 as a Diagnostic Biomarker for Bacterial Infection in Critically Ill Patients As previously noted, EBI3 had the highest predictive strength for bacterial infection in critically ill children. EBI3 is a subunit of IL-27, a heterodimeric cytokine produced by antigen presenting cells which plays a role in regulating T-cell function (Wojno, et al. Trends in Immunol. 33:91-7 (2012)). Since IL-27 protein concentrations can be readily measured in the serum compartment, IL-27 serum protein concentrations were tested as a diagnostic biomarker for infection in critically ill patients.

IL-27 serum protein concentrations were measured in a cohort of 231 critically ill children. Of this cohort, 101 patients met criteria for SIRS and had negative bacterial cultures, 38 met criteria for sepsis and had positive bacterial cultures, and 92 met criteria for septic shock and had positive bacterial cultures. All serum samples represented the first 24 hours of meeting clinical criteria for SIRS, sepsis, or septic shock. The basic clinical and demographic characteristics of this cohort and the respective median IL-27 concentrations are shown in Table 4. Patients with SIRS had significantly lower IL-27 serum protein concentrations compared to patients with sepsis and patients with septic shock.

TABLE 4

Clinical characteristics of the IL-27 cohort.

|  | SIRS (n = 101) | Sepsis (n = 38) | Septic Shock (n = 92) |
|---|---|---|---|
| Median Age in Years | 3.8 (1.2-6.4) | 1.3 (0.4-5.3)[1] | 2.4 (0.9-5.8) |
| Males (%) | 58 | 58 | 64 |
| Median PRISM Score | 7 (2-11) | 7 (5-13) | 14 (8-21)[2] |
| Mortality (%) | 0 | 5 | 143 |
| Median IL-27 (ng/ml) | 2.5 (1.6-3.7)[4] | 6.1 (3.6-9.5) | 5.9 (3.2-10.9) |
| Median PCT (ng/ml) | 1.3 (0.1-2.4) | 1.8 (0.1-4.9) | 6.1 (2.7-20.5)[2] |

[1]$p < 0.05$ vs. SIRS.
[2]$p < 0.05$ vs. SIRS and sepsis
[3]$p < 0.05$ vs. SIRS
[4]$p < 0.05$ vs. sepsis and septic shock To determine the ability of serum IL-27 concentrations to predict bacterial infection in critically ill patients, the patients with sepsis and septic shock were grouped as positive cases for infection and were compared to the SIRS patients as negative cases for infection. The area under the curve (AUC) for the receiver operating characteristic (ROC) curve was 0.813. The IL-27 test characteristics for predicting infection in critically ill patients are provided in Table 5.

TABLE 5

IL-27 test characteristics for predicting bacterial infection.

| Cut-off point≥ (ng/ml) | Sensitivity | Specificity | Positive Predictive Value | Negative Predictive Value |
|---|---|---|---|---|
| 2 | 92 (86-96) | 35 (26-45) | 65 (58-72) | 78 (62-88) |
| 3 | 79 (71-86) | 60 (50-70) | 72 (64-79) | 69 (58-78) |
| 4 | 69 (61-77) | 82 (73-89) | 83 (75-90) | 67 (58-75) |
| 5 | 61 (52-69) | 92 (84-96) | 91 (82-96) | 64 (56-72) |
| 6 | 51 (42-60) | 96 (89-99) | 94 (85-98) | 60 (52-68) |

At a cut-off point of ≥5.0 ng/ml, serum IL-27 was found to have a >90% specificity and positive predictive value (PPV) for bacterial infection in critically ill patients. Collectively, these data indicate that serum IL-27 can potentially serve as an effective "rule-in" test for bacterial infection in critically ill patients.

Example 5

Comparison to Procalcitonin

Since procalcitonin (PCT) is currently being used clinically as a biomarker for bacterial infection in critically ill patients, serum PCT concentrations were also measured in the same cohort of patients. As shown in Table 1, patients with septic shock had significantly higher PCT concentrations as compared to patients with SIRS or sepsis. PCT concentrations yielded an AUC of 0.743 ($p=0.049$ vs. the AUC for IL-27). The PCT test characteristics for predicting infection in critically patients are provided in Table 6. These data demonstrate that IL-27 generally performs better than PCT for predicting infection in critically ill patients.

TABLE 6

PCT test characteristics for predicting bacterial infection.

| Cut-off point≥ (ng/ml) | Sensitivity | Specificity | Positive Predictive Value | Negative Predictive Value |
|---|---|---|---|---|
| 0.5 | 88 (81-93) | 30 (21-40) | 62 (55-69) | 67 (51-80) |
| 1 | 85 (77-90) | 37 (28-47) | 64 (56-71) | 65 (51-77) |
| 2 | 70 (61-78) | 62 (52-71) | 70 (62-78) | 61 (51-71) |
| 3 | 63 (54-71) | 82 (73-89) | 82 (73-89) | 63 (54-71) |
| 4 | 56 (47-65) | 87 (78-93) | 85 (75-91) | 60 (52-68) |

Example 6

Combining IL-27 and PCT

Figure 2:
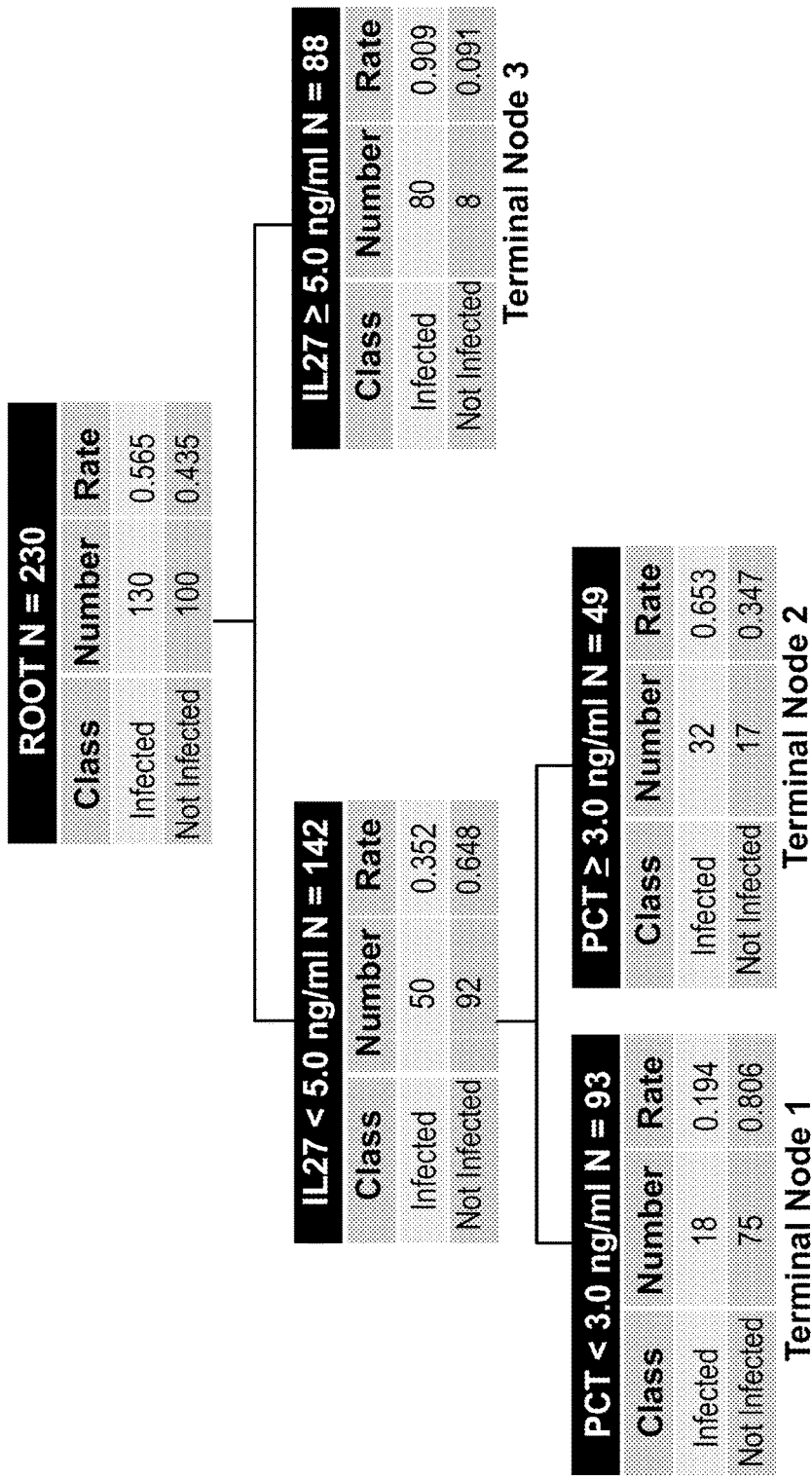
FIG. 2 depicts a CART-generated decision tree combining IL-27 and PCT for the prediction of bacterial infection in critically ill patients. Each node provides the total number of patients in either the sepsis ("Infected") or SIRS ("Not Infected") classes, along with the respective rates. Each node also provides the decision rule based on either an IL-27 or a PCT concentration cut-off point. The decision tree generated three terminal nodes having variable risks for infection.

CART analysis was then conducted to determine if a combination of serum IL-27 and PCT concentrations could further improve the ability to predict infection in critically ill patients (Muller, et al. *Clin. Chian. Acta* 394:1-6 (2008)). The optimized decision tree generated by CART analysis is shown in FIG. 2. The decision tree consists of two decision rules and three terminal nodes. Subjects in terminal node 1 had a 19.4% risk of infection. Subjects in terminal nodes 2 and 3 had a 65.3% and a 90.9% risk of infection, respectively.

To calculate the test characteristics of the decision tree, all subjects in terminal node 1 were classified as "not infected," and all subjects in terminal nodes 2 and 3 were classified as "infected." This approach yielded an AUC of 0.846, a sensitivity of 85% (79-91), a specificity of 75% (65-83); a positive predictive value of 82% (74-88), and a negative predictive value of 81% (71-88). Collectively, these data demonstrate that a combination of IL-27 and PCT improves the overall ability to predict infection in critically ill patients, compared to either biomarker alone.

Example 7

Use of IL-27 as Biomarker to Diagnose Bacterial Infection in Critically Ill Patients IL-27 was selected as a candidate diagnostic marker in an objective manner, using the discovery potential of transcriptomics. In addition, the study cohort was relatively large, and all patients in the sepsis cohort had formal microbiological confirmation of bacterial infection. Further, the study cohort represented patients from 17 different institutions. Finally, the serum IL-27 data reflect the first 24 hours of meeting criteria for SIRS/sepsis, which is a clinically relevant time point for the prediction of bacterial infection in critically ill patients.

Serum IL-27 protein levels ≥5 ng/ml, obtained within the first 24 hours of meeting clinical criteria for SIRS/sepsis had high specificity and a high positive predictive value for predicting bacterial infection in the study cohort of over 200 critically ill patients with SIRS or sepsis. Thus, serum IL-27 can serve as an effective "rule-in" test given that concentrations ≥5 ng/ml had a >90% specificity and positive predictive value for bacterial infection in this cohort of critically ill patients. Conversely, serum IL-27 protein concentrations <5 ng/ml do not necessarily rule out bacterial infection given that the negative predictive value for a concentration <2 ng/ml was 78%. Finally, it does not appear that increased IL-27 protein concentration in critically ill patients with bacterial infection reflects increased illness severity because the median IL-27 concentrations were similar between patients with sepsis and patients with septic shock.

The diagnostic method is carried out on a patient to determine if a critically ill patient has a bacterial infection. A serum sample is obtained from a critically ill patient. Serum IL-27 protein concentration is then measured (e.g. using a magnetic bead multi-plex platform and a Luminex® 100/200 System). The IL-27 protein concentration result is then used in order to establish a diagnosis of bacterial infection.

Example 8

Use of IL-27 in Combination With PCT as Biomarkers to Diagnose Bacterial Infection in Critically Ill Patients PCT has emerged as the predominant diagnostic biomarker for bacterial infection in the clinical setting. However, the diagnostic performance of PCT varies depending on the patient population in which it is applied, and a meta-analysis by Tang et al. concluded that PCT does not reliably differentiate sepsis from non-infectious causes of SIRS in critically ill adults (Tang, et al. *The Lancet Infectious Diseases* 7:210-7 (2007)). In the present study population, IL-27 generally performed better than PCT based on the AUC and the test characteristics calculated for various cut points.

Given the biological complexity and heterogeneity of critical illness, it is unlikely that any one biomarker will consistently predict the presence of bacterial infection. Accordingly, a strategy that combines diagnostic biomarkers may perform better than any single biomarker (Sutherland, et al. *Crit. Care* 15:R149 (2011)). Use of a combination of IL-27 and PCT demonstrated an improved ability to both "rule-in" and "rule-out" bacterial infection in this cohort of critically ill patients.

The diagnostic method is carried out on a patient to determine if a critically ill patient has a bacterial infection. A serum sample is obtained from a critically ill patient. Serum IL-27 protein concentration and PCT protein concentration are then measured (e.g. using a magnetic bead multi-plex platform and a Luminex® 100/200 System). The IL-27 and PCT protein concentration results are then used in combination in order to establish a diagnosis of bacterial infection.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for diagnosing and treating sepsis in a critically ill patient presenting with fever and other signs of a systemic inflammatory response syndrome (SIRS) comprising:
    obtaining a serum sample from the patient, wherein the serum sample is obtained from the patient within the first 24 hours of the patient meeting the clinical criterial for SIRS or sepsis;
    measuring serum interleukin 27 (IL-27) protein concentration in said sample;
    diagnosing the patient with sepsis when the serum IL-27 protein concentration is 5 ng/ml or higher, and
    administering one or more antibiotics to the diagnosed patient.

2. The method of claim 1, wherein the IL-27 protein concentration of 5 ng/ml or higher provides a diagnosis of bacterial infection in a critically ill patient with greater than 80% specificity and/or greater than 80% positive predictive value.

3. The method of claim 1, wherein the IL-27 protein concentration of 5 ng/ml or higher provides a diagnosis of bacterial infection in a critically ill patient with greater than 90% specificity and/or greater than 90% positive predictive value.

4. The method of claim 1, wherein procalcitonin (PCT) concentration is also measured, and wherein said IL-27 and said PCT protein concentration results are used in combination to differentiate sterile inflammation and bacterial infection in said patient.

5. A method for treating a critically ill patient presenting with fever and other signs of a systemic inflammatory response syndrome (SIRS) or sepsis comprising:
    obtaining a serum sample from the patient;
    measuring serum IL-27 protein concentration and procalcitonin (PCT) in said sample;
    diagnosing the patient with sepsis when the serum IL-27 protein concentration is 5 ng/ml or higher, and administering one or more antibiotics to the patient diagnosed with sepsis;
    diagnosing the patient with SIRS when the serum IL-27 protein concentration is less than 5 ng/ml and the PCT concentration is less than 3 ng/ml; and
    treating the patient diagnosed with SIRS with an SIRS therapy selected from one or more of intubation, supplemental oxygen, assisted ventilation, fluid and electrolyte resuscitation, surgical procedures, kidney dialysis, and blood pressure medication.

6. The method of claim 5, wherein IL-27 protein concentration of 5 ng/ml or higher provides a diagnosis of bacterial infection in a critically ill patient with greater than 80% specificity and/or greater than 80% positive predictive value.

7. The method of claim 5, wherein IL-27 protein concentration of 5 ng/ml or higher provides a diagnosis of bacterial infection in a critically ill patient with greater than 90% specificity and/or greater than 90% positive predictive value.

8. The method of claim 5, wherein PCT concentration of less than 3 ng/ml provides a diagnosis of sterile inflammation in a critically ill patient with greater than 80% specificity and/or greater than 80% positive predictive value.

9. A method for diagnosing and treating a bacterial infection in a human patient in need thereof, the method comprising determining the amount of IL-27 protein in a serum sample from the patient, diagnosing the patient with a bacterial infection when the serum IL-27 protein concentration is 5 ng/ml or higher, and administering one or more antibiotics to the diagnosed patient.

10. The method of claim 9, wherein the patient displays clinical signs of a systemic inflammatory response (SIRS) or sepsis.

11. The method of claim 10, wherein the serum sample is obtained from the patient within the first 24 hours of the patient meeting the clinical criterial for SIRS or sepsis.

12. The method of claim 11, wherein the amount of IL-27 protein in the serum sample is determined using flow cytometry.

13. The method of claim 12, further comprising determining the amount of procalcitonin in the serum sample.

14. The method of claim 1, wherein the one or more antibiotics is selected from the group consisting of cefotaxime, ticarcillin-clavulanate, piperacillin-tazobactam, imipenem-cilastatin, meropenem, clindamycin, metronidazole, ceftriaxone, ciprofloxacin, cefepime, levofloxacin, and vanomycin.

15. The method of claim 5, wherein the one or more antibiotics is selected from the group consisting of cefotaxime, ticarcillin-clavulanate, piperacillin-tazobactam, imipenem-cilastatin, meropenem, clindamycin, metronidazole, ceftriaxone, ciprofloxacin, cefepime, levofloxacin, and vanomycin.

* * * * *